United States Patent [19]

Linnarsson et al.

[11] Patent Number: 4,608,995
[45] Date of Patent: Sep. 2, 1986

[54] METHOD AND APPARATUS FOR THE NON-INVASIVE DETERMINATION OF THE MINUTE VOLUME OF THE HEART

[75] Inventors: Dag Linnarsson, Stocksund; Hans Larsson, Stockholm, both of Sweden

[73] Assignee: Karolinska Institutet Institutionen för Medicinsk Teknik, Stockholm, Sweden

[21] Appl. No.: 640,662

[22] Filed: Aug. 14, 1984

[30] Foreign Application Priority Data

Jan. 19, 1983 [SE] Sweden ................................ 8300246

[51] Int. Cl.$^4$ .............................................. A61B 5/02
[52] U.S. Cl. .................................... 128/713; 128/719; 128/725
[58] Field of Search ................ 128/713, 691, 718–719, 128/725–729, 671, 670

[56] References Cited

U.S. PATENT DOCUMENTS

| | | | |
|---|---|---|---|
| 4,083,367 | 4/1978 | Portner et al. | 128/691 |
| 4,169,465 | 10/1979 | Walls et al. | 128/719 |
| 4,363,327 | 12/1982 | Clark | 128/719 |
| 4,463,764 | 8/1984 | Anderson et al. | 128/719 |

*Primary Examiner*—Kyle L. Howell
*Assistant Examiner*—Angela D. Sykes
*Attorney, Agent, or Firm*—Hammond & Littell, Weissenberger & Dippert

[57] ABSTRACT

An arrangement for the non-invasive determination of the minute volume $\dot{Q}$ of the heart is arranged to determine the amount of a sufficiently soluble gas, e.g. carbon dioxide or nitrous oxide, present in the blood, prior to and subsequent to the passage of the blood through the heart. The expired and inspired gases are separated from one another with each breath taken. Transducers feed respective devices for determining the gas content of the respiration gas, and the magnitude of the expiration gas flow and the inspiration gas flow. These devices are controlled by a microprocessor, which is programmed to supply gas from a gas source, to meter the gas during a subsequent inspiration cycle, and to control an indicator for the $\dot{Q}$-value. The gas is controlled in a manner such that the gas-content of the lungs is changed in accordance with a given program. The $\dot{Q}$-value is calculated for pairs of respiration cycles in accordance with the formula:

$$\dot{Q} = \frac{\dot{V}_1 - \dot{V}_2}{Ca_1 - Ca_2}$$

in which
$\dot{V}_1$ is the effective gas flow/unit time for a respiration cycle;
$\dot{V}_2$ is the effective gas flow/unit time for the next respiration cycle;
$Ca_1$ is the gas content of arterial blood for the first respiration cycle;
$Ca_2$ is the gas content of arterial blood for the next respiration cycle.

The microprocessor is arranged to calculate $\dot{Q}$ for a plurality of pairs of respiration cycles (e.g. 5–6 pairs) with a given number of respiration cycles therebetween (e.g. 4), and to send to the indicator a signal corresponding to the mean value of the $\dot{Q}$-values obtained.

8 Claims, 11 Drawing Figures

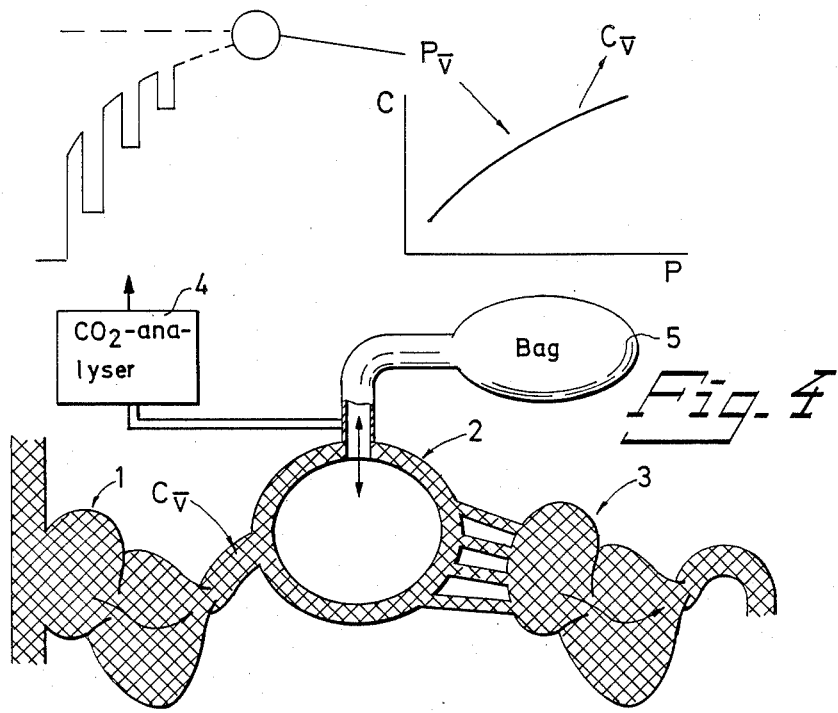
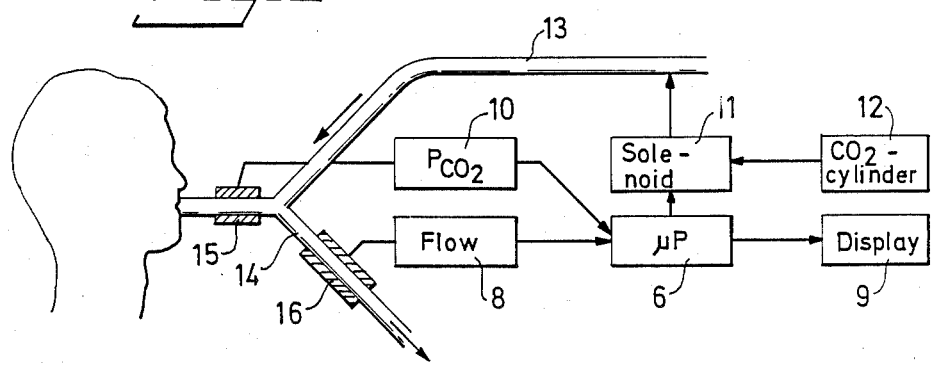

METHOD AND APPARATUS FOR THE NON-INVASIVE DETERMINATION OF THE MINUTE VOLUME OF THE HEART

SUMMARY OF THE INVENTION

The present invention relates to a method for the non-invasive determination of the minute volume $\dot{Q}$ of the heart, which method comprises the steps of estimating the amount in which a sufficiently soluble gas is present in the blood, prior to and subsequent to passage of the blood through the lungs; separating the expired gas from the inspired gas with each breath and measuring directly in the flow of respiration gas the magnitude of said respiration gas flow and the amount of said soluble gas contained therein and optionally using the determined values of said flow magnitude and said soluble gas content during expiration for the controlled metering of said soluble gas to the flow of inspiration gas from a source of such gas, during the next following inspiration cycle. The invention also relates to apparatus for carrying out the method.

Various known methods for determining the minute volume of the heart are described in a work entitled "Medicin och Teknik", by Bertil Jacobson, second edition, Studentlitteratur, Lund 1975, pages 179–182. The methods described in this work are the Ficks method, the indicator-dilution method and the thermodilution method. These three methods are all so-called invasive methods, i.e., they require catheters to be inserted into blood vessels, blood samples to be taken, and various substances to be injected into the bloodstream, etc. These methods will be discussed hereinafter, together with the non-invasive, or non-haematological methods, to which latter methods the invention relates.

BRIEF DESCRIPTION OF THE DRAWINGS

The following description is made with reference to the accompanying drawings, in which

FIG. 4, 4a, and 4b represent a second stage in this method;

FIG. 5 illustrates a method according to the invention;

DESCRIPTION OF THE PREFERRED EMBODIMENTS

Figure 1:
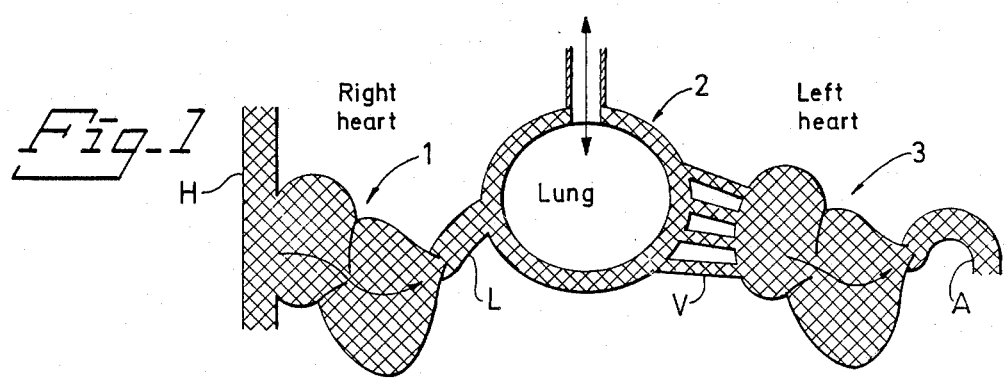
FIG. 1 is a schematic illustration of that path of the path travelled by the blood which includes the heart and lungs.

When the body of a human being is at rest, the heart will pump about 5 liters of blood per minute (beat volume ca 75 ml, beat frequency ca 70 beats/minute). When the body is subjected to strenuous, muscular activities, the volume of blood pumped each minute by the heart (normally referred to as the minute volume of the heart) can reach 25 ml, whereupon both the beat volume and the beat frequency are increased by a factor of from 2 to 3. Normally, the blood passes through the right-hand side 1 of the heart, the lungs 2, and the left-hand side 3 of the heart, in that order. The heart minute volume can be defined as the flow of blood 2, from or through any one of these sections of the central circuit travelled by the blood.

FIG. 1 illustrates schematically, from left to right, the right-hand side 1 of the heart, the lungs 2, and the left-hand side 3 of the heart. The upper and lower afferent blood vessels H conduct blood rich in carbon dioxide to the right-hand auricle, this blood being conducted from the right-hand chamber to the lung 2, via the lung artery L. During respiration, carbon dioxide is given-off in the lung (the upper arrowhead of the double-arrow) and oxygen is taken-up (the lower arrowhead). Blood enriched with oxygen passes via the lung arteries V to the left-hand auricle and left-hand chamber, from where it passes out into the aorta A and into the body.

The heart minute volume is an extremely important parameter in determining the seriousness of a patient's condition, for example, in conjunction with the state of shock of a patient and with major surgical or operative work, etc.

The heart minute volume is also an extremely important variable for study in those sections of medicine concerned with the effects of manual labour, sporting activities, re-habilitation, and the like, in which it is desired to determine which factors influence the physical working ability of the human body.

Figure 2:
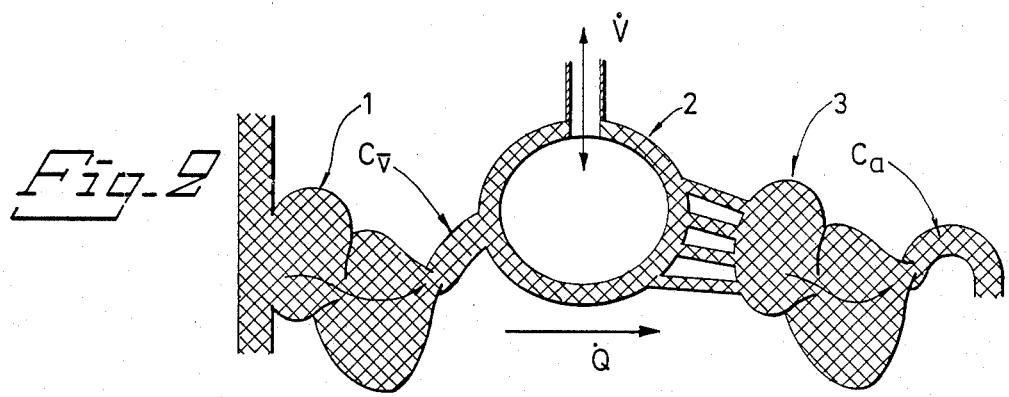
FIG. 2 illustrates the blood path shown in FIG. 1, but with parameters utilized in accordance with the invention inserted.

Conventionally, the minute volume of the heart is determined by invasive methods (haematological-methods), which involve the insertion of catheters into the bloodstream. Such procedures expose the patient to a certain amount of risk and to a degree of discomfort, these matters being weighed against the fact that the minute volume of the patient's heart can be determined through application of the invasive method, and the necessary treatment can be decided in consequence thereof. Normally, the invasive method involves inserting a catheter, via a vein, through the right-hand side 1 of the heart and into the lung artery L, and injecting an indicator liquid thereinto (thermodilution), this liquid normally comprising a cooking salt solution. A more complicated method is one in which peripheral arteries are punctured to enable samples to be taken, and a pigment is injected on the vein side (pigment solution). In the oldest and most complicated method used, catheters are placed in both the lung artery L and a peripheral artery, and samples are taken of the oxygen content of both mixed vein blood and artery blood, while simultaneously determining the amount of oxygen taken-up by the lungs. These determining methods are carried out in accordance with the Ficks principle and are illustrated in FIG. 2.

The following formuli apply in this respect:

$$\dot{V} = \dot{Q} \cdot C_{\bar{v}} - \dot{Q} \cdot C_a \qquad \text{(Equ. 1)}$$

$$\dot{Q} = \frac{\dot{V}}{C_{\bar{v}} - C_a}$$

where
$\dot{V}$ = oxygen absorbed (ml $O_2$/min)
$\dot{Q}$ = the flow rate of the blood through the lungs (in liters of blood per minute)
$C_{\bar{v}}$ = the oxygen content of mixed vein blood (ml $O_2$/l blood)
$C_a$ = the oxygen content of artery blood (ml $O_2$/l blood)

In principle, similar calculations can be made just as well on the basis of the carbon dioxide contained in the blood. In this case $\dot{V}$ represents the amount of carbon dioxide given out, while $C_{\bar{v}}$ and $C_a$ each represent the carbon dioxide content of blood.

In addition to these methods, the minute volume of the heart can also be determined by noninvasive methods, as previously mentioned. A common feature of these methods is that Q is determined on the basis of the values of $C_{\bar{v}}$ and $C_a$, estimated without taking blood samples. $\dot{V}$ is always determined non-invasively, by collecting and analyzing expiration gas. $\dot{Q}$ is then calculated in accordance with Ficks principle. The estimation of $C_{\bar{v}}$ and $C_a$ is encumbered with certain error sources, which are smaller when the calculations are made on the basis of the amount of carbon dioxide given out than when made on the amount of oxygen absorbed. This is because carbon dioxide passes more easily between the lungs and the blood, and because the $CO_2$-content of the blood has a relatively simple relationship to the $CO_2$-content of the gas in the lungs.

Figure 3A:
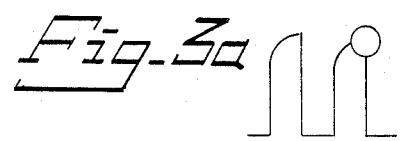
FIG. 3, 3a, and 3b represent a known non-invasive method for determining the minute volume of the heart.
Figure 3B:
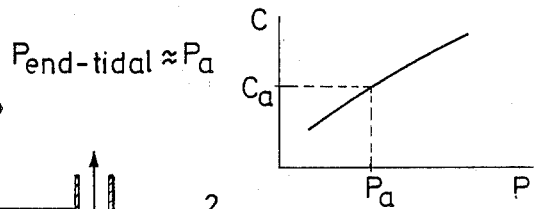
Figure 3:
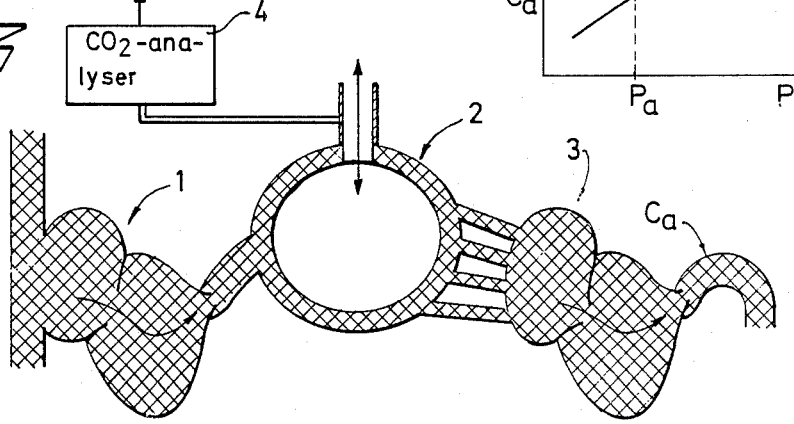
Figure 6:
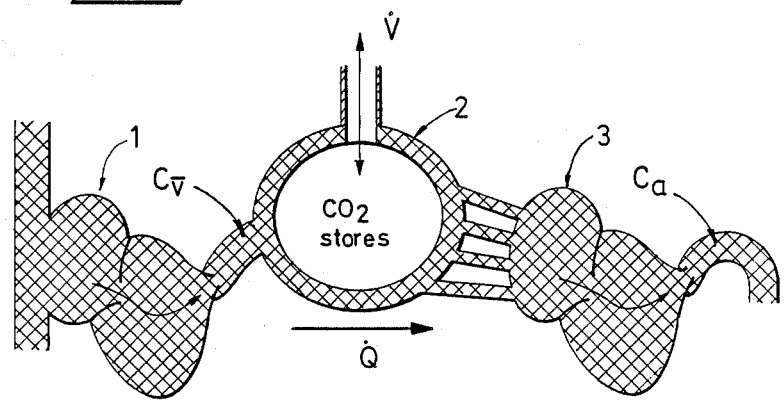
FIG. 6 illustrates parts of the blood circulatory system, with certain parameters inserted.

Non-invasive determination of the heart minute volume on the basis of the $CO_2$-yield between blood and lungs is a methodology which has long been known to the art. It is a complicated method, which requires the cooperation of the patient and the use of bulky equipment. The method is carried out in two stages, and requires the gas yield and heart minute volume to be stable for several minutes. In this respect, the amount of carbon dioxide given out is determined first. Referring to FIG. 3, the peak-concentration of carbon dioxide expired is measured with the aid of a rapid $CO_2$-analyser 4. This peak-concentration, which is illustrated in the curve shown in FIG. 3a and which is often the mean value for a multiplicity of respiration cycles, is converted to partial pressure ($P_{end-tidal}$), said value being approximately equal to the carbon-dioxide partial-pressure prevailing in the arterial blood ($P_a$). $C_a$, i.e., the $CO_2$-content of the arterialized blood leaving the lungs, is then calculated on the basis of a standardized, non-linear relationship between partial pressure (P) and the volumetric content (C) of $CO_2$ in blood. See, in this respect, the diagram in FIG. 3b. The $CO_2$-content of the mixed venous blood is then calculated, in the second stage of the method. The patient re-breathes 1-2 l/breath in a bladder 5, whereupon the partial pressure of carbon dioxide in the bladder and in the lungs rises asymptotically towards the same value $P_{\bar{v}}$ as that found in the blood rich in carbon dioxide entering the lungs. Re-breathing takes about 20 seconds. cf. FIGS. 4, 4a, and 4b.

The aforedescribed method is encumbered with a number of disadvantages.
Practical: it requires the cooperation of the patient; the use of complicated apparatus equipped with large mechanical valves; and precise filling of the re-breathing bladder 5.
Medicinal/hygienical: risk of oxygen deficiency during re-inspiration, even when there is initially a surplus of oxygen in the bladder 5. The unhygienic inspiration of expired gas.
Theory/calculation: the estimation of $C_a$ from an expired peak concentration is based on a number of precarious assumptions. The estimation of $C_{\bar{v}}$ on the basis of extrapolation is still more precarious. The assumption that all carbon dioxide leaving the blood to the lungs always departs from the lungs to the surroundings is not positive; $CO_2$ can be stored in the lung tissue.

The object of the invention is to eliminate these disadvantages. The method according to the invention includes two procedural steps which are novel in principle and which are characteristic of the invention.

A. The re-breathing bladder is replaced with an electronic system arranged to measure the amount of carbon dioxide expired and to then meter a corresponding amount of carbon dioxide to the inspiration gas in a subsequent respiration cycle (FIG. 5). In this way, selective re-breathing of solely *one* gas component is achieved, and there is provided a more positive and simpler method of carrying out this stage in the conventional re-breathing methodology illustrated in and described with reference to FIG. 4.

The apparatus arrangement illustrated in FIG. 5 includes an inspiration tube 13 and an expiration tube 14. A transducer 15 is connected to a means 10 for measuring the $CO_2$-content of the expiration gas ($P_{CO_2}$). A further transducer 16 is connected to a means 8 for measuring the expiration flow. A $CO_2$-source 12 is connected to a solenoid 11, which is controlled by a microprocessor ($\mu P$) 6 for metering carbon dioxide to the inspiration tube 13. The means 8 and 10 control the microprocessor 6, which in turn controls an indicating means 9. The expiration and inspiration gases are mutually separated by means of respiration valves. The expiration flow and the $CO_2$-content of the expiration gas is measured directly in the respiration flow by means of transducers 15, 16. The microprocessor 6 ($\mu P$) is arranged to calculate the amount of carbon dioxide expired, and controls the metering process in a manner such that equally large quantities are metered to the inspiration gas during a subsequent respiration cycle.

B. The second principly procedural step of the invention comprises a novel method of calculation, made possible by the arrangement of apparatus illustrated in FIG. 5, when said arrangement is modified with respect to its gas-metering function.

The method according to the invention is characterized by controlling the metering of said gas in a manner such that the gas-content of the lungs is changed in accordance with a given programme (for example, a linear increase with respect to time); and by determining the value $\dot{Q}$ for pairs of respiration cycles as the ratio between the difference between effective gas flow/unit of time $\dot{V}_1$ for one respiration cycle and $\dot{V}_2$ for the next respiration cycle and the difference between the gas content $Ca_1$ and $Ca_2$ respectively in arterial blood; by determining the value $\dot{Q}$ for a plurality of pairs of respiration cycles, said pairs being spaced by a given number of respiration cycles; and by calculating the mean value of the various values of $\dot{Q}$ obtained.

The arrangement according to the invention is mainly characterized by a microprocessor which is programmed to control the gas-metering function in a manner such as to change the gas-content of the lungs in accordance with a given programme, and which is arranged to determine $\dot{Q}$ for pairs of respiration cycles in accordance with the formula $$\dot{Q} = \frac{\dot{V}_1 - \dot{V}_2}{Ca_1 - Ca_2} \qquad \text{(Equ. 4)}$$

in which $\dot{V}$ is the effective gas flow per unit of time calculated breath for breath, and Ca is the simultaneously calculated gas-content per unit of arterial blood, the index 1 signifying a first respiration cycle and the index 2 signifying a following respiration cycle, and the microprocessor calculating $\dot{Q}$ for each number of pairs of respiration cycles, said pairs being spaced apart by a given number of pairs of respiration cycles, and determining the mean value of the various values of $\dot{Q}$ thus obtained.

$\dot{V}$ signifies in this case the effective flow of carbon dioxide per unit of time, calculated breath for breath, i.e., (the amount of $CO_2$ inspired—the amount of $CO_2$ expired)/time with each breath. The value $\dot{V}_1$ is obtained for each breath, and a mass-balance equation for the flows of carbon dioxide can be compiled;

$$C_{\bar{v}} \cdot \dot{Q} = \dot{V}_1 + Ca_1 \cdot Q + \Delta - \text{storage} \qquad \text{(Equ. 2)}$$

$Ca_1$ is the simultaneously calculated $CO_2$-content of artery blood. During a later respiration cycle (breath), the value $V_2$ prevails, together with a further, higher value of Ca ($Ca_2$). A second mass-balance equation can then be compiled.

$$C_{\bar{v}} \cdot Q = \dot{V}_2 + Ca_2 \cdot Q + \Delta - \text{storage} \qquad \text{(Equ. 3)}$$

With regard to definition, Q and $C_{\bar{v}}$ remain unchanged during the short period of time between the two respiration cycles or breaths, this period being in the order of about two seconds. The term "$\Delta$—storage" is necessitated by the continuously increasing $CO_2$-content of the lungs. The two equations are subtracted, and a simple mathematical expression is then obtained from which $\dot{Q}$ can be calculated (cf. Equation 4 above). The calculation is repeated for 5 or 6 pairs of respiration cycles, which are separated pairwise by four respiration cycles, for example. The mean value of $\dot{Q}$ is then calculated. The whole of the measuring procedure is effected in a single stage, taking less than about 20 seconds.

Figure 7:
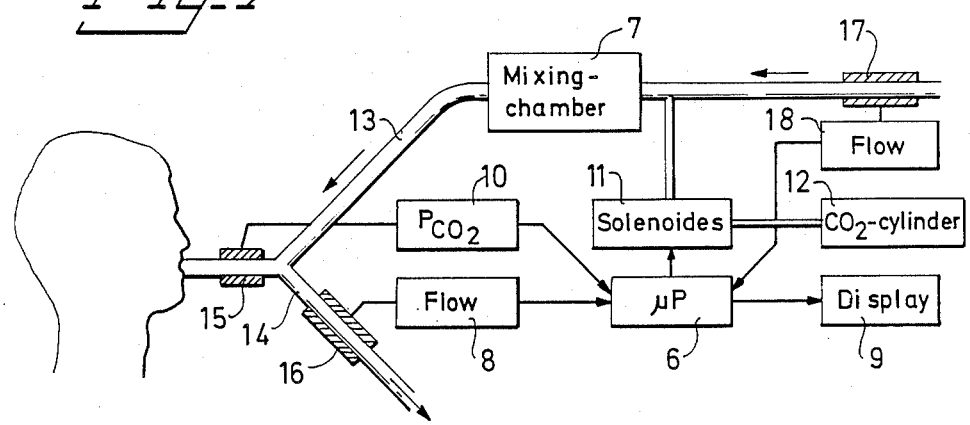
FIG. 7 illustrates an arrangement of apparatus according to the invention.

The aforementioned disadvantages encountered with the known technique with regard to theory and calculation are eliminated to a very large extent when practicing the present invention. The estimation of $C_a$ is still encumbered with an error risk, but since two values having the same error risk are subtracted, one from the other, the risk becomes nonexistent. It is *not* necessary to extrapolate $C_{\bar{v}}$, since $C_{\bar{v}}$ is not included in the final calculation. FIG. 7 illustrates a further, slightly more complicated version which can be used for the same calculating procedure as that illustrated in FIG. 5. The arrangement of apparatus illustrated in FIG. 7 includes a flow meter 18, which also measures the flow of inspiration gas, and a mixing chamber 7 which is cooperative in metering carbon dioxide. This enables the metering of pure carbon dioxide to be sychronized with the flow of inspiration gas, so as to obtain a uniform mixture, even when breathing is irregular. The carbon dioxide is metered by means of a group of solenoid valves, the opening frequency and opening time of which determines the amount of carbon dioxide metered. When metered, the carbon dioxide gas supplied can be mixed with oxygen, to avoid lowering the oxygen content of the inspiration gas in conjunction with supplying carbon dioxide. A maximum of 8% carbon dioxide is reached in the lung gas.

In the variant illustrated in FIG. 7, the elements 6 and 8-16 are the same as those in the FIG. 5 embodiment. The additional devices include the flow meter 18 for measuring the inspiration gas, a transducer 17, and a mixing chamber 7. The flow meter 18, and the devices 8 and 10 control the microprocessor 6, which controls the amount of carbon dioxide supplied to the inspiration gas, as with the FIG. 5 embodiment.

The FIG. 7 embodiment may also be used with nitrous oxide ($N_2O$), or some other gas which is sufficiently soluble in the blood, instead of carbon dioxide. Nitrous oxide when administered in minor concentrations will not affect the consciousness of the patient, and has the advantage of not stimulating breathing and giving the sensation of breathlessness in the same manner as carbon dioxide.

We claim:

1. A method for the non-invasive determination of the minute volume $\dot{Q}$ of the heart of a subject, which method comprises the steps of (a) estimating the amount in which a sufficiently soluble gas is present in the blood of the subject, prior to and subsequent to the passage of the blood through the heart; (b) separating expired gas from inspired gas with each respiration cycle and measuring directly in the flow of respiration gas the magnitude of said respiration gas flow and the amount of said soluble gas contained therein; and (c) using the determined values of said flow magnitude and said soluble-gas content to control metering of said soluble gas to the flow of inspiration gas from a source of such gas during the next following cycle, wherein the metering of said soluble gas is controlled in a manner to change the lung content of said gas in accordance with a given program; the value $\dot{Q}$ for pairs of respiration cycles is determined as the ratio between the difference between (i) effective gas-flow/unit time $\dot{V}_1$ for each respiration cycle and $\dot{V}_2$ for the next respiration cycle and (ii) the difference between the gas-content in arterial blood $Ca_1$ for each respiration cycle and $Ca_2$ for the next respiration cycle; $\dot{Q}$ for a plurality of pairs of respiration cycles is determined, each pair of said cycles being spaced by a given number of respiration cycles; and the mean value of $\dot{Q}$ is calculated from the various values $\dot{Q}$ determined.

2. The method of claim 1, wherein the soluble gas is carbon dioxide.

3. The method of claim 1, wherein the soluble gas is nitrous oxide.

4. The method of claim 1, wherein said program provides a linear increase in the amount of said gas contained in the lung gas by increasing the amount of said gas inspired with each respiration cycle.

5. The method of claim 1, wherein a microprocessor is controlled through a first transducer means for measuring the amount of said soluble gas in the respiratory gas, through a second transducer means for measuring the flow in the expiration gas, and through a third transducer means for measuring the flow of inspiration gas, and the microprocessor is programmed to control, as a function of the values measured by said transducer means, valve means for supplying said gas from a source thereof to a mixing chamber, to which inspiration gas is also supplied.

6. An apparatus for the non-invasive determination of the minute volume $\dot{Q}$ of the heart, said apparatus comprising means for separating expired gas from inspired gas at each respiration cycle, means for measuring the magnitude of the expired gas flow, means for determining the content of the soluble gas in the respiration flow, means controlled by said flow-measuring and content-determining means for metering said gas to the flow of inspiration gas from a gas source during the next following inspiration cycle, wherein a microprocessor is programmed to control the gas-metering process in a manner such that the lung content of said gas is changed in accordance with a given program and is arranged to determine $\dot{Q}$ for pairs of respiration cycles in accordance with the formula $$\dot{Q} = \frac{\dot{V}_1 - \dot{V}_2}{Ca_1 - Ca_2}$$

in which V is the effective gas flow per unit of time, calculated breath for breath, Ca is the simultaneously calculated gas content per unit of arterial blood, the index 1 representing a first respiration cycle and the index 2 representing the next following respiration cycle, and wherein the microprocessor is arranged to calculate $\dot{Q}$ for a plurality of pairs of respiration cycles, said pairs being separated by a given number of respiration cycles, and to determine the mean value of the various values of $\dot{Q}$ obtained.

7. The apparatus of claim 6, wherein the program is arranged to provide a linear increase in the gas content of the lung gas by causing the microprocessor to increase the amount of soluble gas inspired with each breath taken.

8. The apparatus of claim 6, wherein the microprocessor is arranged to be controlled by a first transducer means to determine the gas content; by a second transducer means to determine the flow of expiration gas; and by a third transducer means to determine the flow of inspiration gas, the microprocessor being programmed to control solenoids as a function of the output signals on said means, said solenoids functioning as valves between a gas source and a mixing chamber supplied with said inspiration gas and said soluble gas, and wherein the microprocessor is arranged to control an indicating means to indicate the value of $\dot{Q}$.

* * * * *

UNITED STATES PATENT AND TRADEMARK OFFICE
CERTIFICATE OF CORRECTION

PATENT NO. : 4,608,995

DATED : September 2, 1986

INVENTOR(S) : DAG LINNARSSON et al.

It is certified that error appears in the above-identified patent and that said Letters Patent is hereby corrected as shown below:

Column 1, line 40, "path" should read -- part --.

Signed and Sealed this

Eleventh Day of November, 1986

*Attest:*

DONALD J. QUIGG

*Attesting Officer*  *Commissioner of Patents and Trademarks*